United States Patent [19]

deCastro et al.

[11] Patent Number: 5,188,941
[45] Date of Patent: Feb. 23, 1993

[54] ENZYMATIC DETERMINATION OF THEOPHYLLINE

[75] Inventors: Aurora F. deCastro, Union, Mich.; Surendra K. Gupta; Arun K. Agarwal, both of Elkhart, Ind.

[73] Assignee: GDS Technology, Inc., Elkhart, Ind.

[21] Appl. No.: 815,590

[22] Filed: Dec. 31, 1991

Related U.S. Application Data

[63] Continuation of Ser. No. 572,203, Aug. 23, 1990, which is a continuation-in-part of Ser. No. 155,498, Feb. 12, 1988.

[51] Int. Cl.$^5$ ............................................. C12Q 1/44
[52] U.S. Cl. ..................................... 435/19; 435/25; 435/26; 435/191; 435/832
[58] Field of Search ................... 435/19, 25, 26, 191, 435/832

[56] References Cited

U.S. PATENT DOCUMENTS

| 4,216,292 | 8/1980 | Tkuta | 435/832 |
| 4,235,869 | 11/1980 | Schwarzberg | 435/7 |
| 4,341,868 | 7/1982 | Nakanishi et al. | 435/191 |

OTHER PUBLICATIONS

Bhargava et al., Engymatic Theophylline Assay . . . , 41st National Meeting of the Am. As. for Clinical Chem., Jul. 23-27, 1989 Clin. Chem. 35(6) 1989 p. 1102.
Gupta et al., A Novel Enpymatic Approach for Serum Theophylline Measurement, 40th Nat. Meeting of the Am. As for Clinical Chem. Jul. 24-28, 1988 Clin. Chem. 34(6) 1988 p. 1267.
Bergomeyer, Methods of Enzymatic Analysis, 3rd ed. vol. III, Xanthine Oxidase p. 211, 1983.
R.A. Robson et al. Characterization of Theophliline Metabolism in Human Liver Microsomes Brit. J. of Clin Pharm. (1987) 24, 293-300.

*Primary Examiner*—Christine M. Nucker
*Assistant Examiner*—Jeffrey Stucker
*Attorney, Agent, or Firm*—Browdy and Neimark

[57] ABSTRACT

The present invention provides a new methodology and test composition for determining the presence of theophylline in test samples. The methodology employs enzymes that utilize or recognize theophylline as a substrate to measure the concentration thereof in samples, including body fluids. This new approach utilizes enzymes as opposed to traditional methods which use antibodies for the recognition of theophylline. The enzymatic approach to theophylline determination is quick, simple and convenient and allows test systems to be made in liquid as well as in dry-chemistry formats. Various protocols, systems or methodologies may be used for assaying and relating the results to the amount of theophylline present. Methods for obtaining theophylline utilizing or recognizing enzymes are also described.

30 Claims, 1 Drawing Sheet

ENZYMATIC DETERMINATION OF THEOPHYLLINE

CROSS REFERENCE TO RELATED APPLICATION

This application is a continuation of application Ser. No. 07/572,203, filed Aug. 23, 1990, which is a continuation-in-part of co-pending application, Ser. No. 07/155,498, filed Feb. 12, 1988.

BACKGROUND OF THE INVENTION

The present invention relates to a method for determining theophylline in a sample. More particularly, the present invention relates to a method for determining theophylline which uses a theophylline utilizing enzyme.

Theophylline is a bronchodilator and respiratory stimulant used in the treatment of patients with asthmatic and allergic conditions. It is also used in the treatment of congestive heart failure and acute pulmonary edema. Benefits, as well as risks, from using this drug directly relate to its serum concentration. In order for the drug to be effective, a concentration of theophylline of about 10–20 mg/L level needs to be maintained in the blood. Theophylline levels of less than 10 mg/L are therapeutically ineffective and levels of more than 20 mg/L may be toxic to the patient. This toxicity may result in brain damage and death. Because the therapeutic advantage of the drug lies only within a narrow range of concentrations and because there is a large interpatient difference in drug elimination due to physiological differences, as well as diet or other prescribed drugs, it is important to monitor patients using this drug.

Theophylline has been measured by gas chromatography by Shah, *J. Pharm. Sci.*, 63(8), 1283 (1974) and by a combination of gas chromatography and mass-selective detector by Desage, et al., *J. Chromat.*, 336(2), 285 (1984). It has been measured by high-pressure liquid chromatography by Thompson, et al., *J. Lab. Clin. Med.*, 84(4), 584 (1974) and by Naish, et al., *Ann. Clin. Biochem.*, 16(5), 254 (1979). Schack, et al., *J. Pharm.*, 97, 283 (1949) used an ultraviolet spectrophotometric method for the determination of theophylline. However, because these methods need cumbersome extractions, most clinical approaches today for the determination of theophylline use immunological methods which depend on antibodies for recognizing theophylline in the sample being tested. Such systems involve competitive protein binding where the antibody is the specific binding protein. After the reaction with antibodies takes place, the determination of theophylline varies depending on the particular assay, that is, the assay readout may be turbidimetric, nephelometric, radioactive or colorimetric depending on whether turbidity, radioactivity or color is produced. Examples of these systems are reported by Painter, et al., *J. Clin. Lab. Autom.*, 3(3), 179 (1983), Samoszuk, et al., *Ther. Drug Mon.*, 5(1), 113 (1983), Opheim, et al., *Clin. Chem.*, 30(11), 1870 (1984), Boeckx and Munson, *Ther. Drug Mon.*, 7(1), 95 (1985), Cook, et al., *Res. Comm. in Chem. Path. & Pharm.*, 13(3), 497 (1976), and Landesman, et al., *Clin. Chem.*, 29, 1238 (1983).

Immunological systems have also been reported by Li et al., *Clin. Chem.*, 27(1), 22 (1981), Davis and Marks, *Ther. Drug Mon.*, 5(4), 479 (1983), Chang, et al., *Clin Chem* 28(2), 361 (1982), Hinds, et al., *Clin. Chem.*, 30(7), 1174 (1984), Jolley, et al., *Clin. Chem.*, 27, 1575 (1983), Morris, et al., *Anal. Chem.*, 53, 658 (1981), and Tyhach, et al., *Clin. Chem.*, 27, 1499 (1981).

In addition, enzymes have been used in an enzyme amplification assay, U.S. Pat. No. 3,817,837. In this disclosure, enzymes are chemically bound to ligands and these enzyme-bound-ligands combine with receptors. The ligand may be a drug. The specific reaction of the ligand with the receptors gives the specificity to the reaction while the enzyme activity is utilized as a marker for the reaction. Therefore, the enzymes used have no enzymatic recognition of the drug. The use of these approaches are totally different to the presently described methodology which uses enzymes instead of antibodies or ligands for the recognition of theophylline.

It has been also reported in European Patent Application Number EP86300226.7, Jan. 15, 1986, as well as in *Clin. Chem.*, 25, 1370 (1979), that the activity of alkaline phosphatase, which acts by cleaving phosphate groups from a substrate, can be inhibited by theophylline. In this approach, the enzymatic reaction of alkaline phosphatase continues to be that of cleaving the phosphate bonds but this action is interfered with by the presence of theophylline. Again, in this disclosure, the theophylline test produced is one in which theophylline is not enzymatically utilized or changed by the enzymatic reaction. By contrast, the present invention teaches that test systems can be produced, using enzymes which utilize or recognize theophylline and use it as a substrate for the quantitation of theophylline in samples.

Since theophylline is a xanthine derivative, commercially available xanthine oxidases and xanthine dehydrogenases and related enzymes were tried for their ability to utilize theophylline and to develop a test system. These attempts were unsuccessful. Although in humans, theophylline is known to be metabolized primarily to 1,3 dimethyluric acid and also to 1 methyluric acid and 3-methylxanthine (Cornish, H. H. and Christman, A. A., *J. Biol. Chem.*, 228, 315 (1957), no theophylline utilizing enzyme has previously been isolated nor its use shown in a test system to quantitate theophylline in a sample.

Here, the present invention contemplates the measurement or quantitation of theophylline concentration using these theophylline utilizing or recognizing enzymes. Examples of these enzymes, namely, theophylline dehydrogenase, theophylline oxidase, and theophylline demethylase are used to demonstrate the efficacy of the method, test composition and test device of the present invention for the measurement of theophylline in samples such as body fluids, food extracts, and medicinal compounds and compositions. The tests that resulted from this enzymatic approach are rapid and convenient to perform. The advantages of the enzymatic approaches are 1) unitized reagent or test composition capability, 2) one step addition of sample to reagent or test composition, 3) a liquid system can be made to perform with instrument readout devices, and 4) the reagent or test composition can easily be incorporated into a solid-phase matrix. The present invention also contemplates a process of obtaining theophylline utilizing or recognizing enzymes from microbial sources which react with theophylline as a substrate and produce a product.

BRIEF DESCRIPTION OF THE DRAWING

The FIGURE shown in the drawing depicts absorbance curves for a theophylline utilizing enzyme before and after contact with theophylline as further described in Example 3.

DESCRIPTION OF THE PREFERRED EMBODIMENTS

The present invention contemplates a method or system for the determination of theophylline by means of a theophylline utilizing or recognizing enzyme or enzymes (or substance containing such enzyme or enzymes) and optionally including the use of electron carriers, as well as a test composition and test device containing or employing such enzyme or enzymes. The present invention also contemplates a method of selecting organisms and finding, isolating, and purifying these enzymes from such organisms. The determination of theophylline using these enzymes is accomplished by measurement of a signal produced by the reaction of the enzyme with any theophylline present in the sample and converting or correlating the amount of signal generated to the concentration of theophylline present in the sample. As used herein, the term "theophylline utilizing enzyme" means an enzyme or substance containing an enzyme which either recognizes or utilizes or reacts with theophylline to produce a signal which by itself or in conjunction with other reagents or means can be measured using visual, instrumental, or other state-of-the-art methodologies and that can be used to measure the concentration of theophylline.

The principle of the test method is based on the utilization of theophylline by an enzyme. That is, the enzyme recognizes theophylline as a substrate and changes it to a different compound or product. Schematically, the system can be described as follows:

theophylline $\xrightarrow{\text{enzyme}}$ Product

As noted above, the methods disclosed and claimed herein involve detecting any signal produced by contact of theophylline with the theophylline utilizing enzyme which indicates that a specific enzymatic reaction has taken place and showing that these signals are directly proportional to the concentration of theophylline in a sample. The signals produced are measured in a variety of ways as described herein. This process occurs in the presence of added electron carriers, either electron acceptors or electron donors. Examples of electron acceptors are oxygen, nicotinamide adenine dinucleotide (NAD), dichlorophenol indophenol (DCPIP), phenzaine methosulfate (PMS), methylene blue, cytochromes, ferricyanide, etc. Examples of electron donors are reduced nicotinamide adenine dinucleotide (NADH), reduced nicotinamide adenine dinucleotide phosphate (NADPH), reduced flavin adenine dinucleotide (FADH), etc.

The process of the present invention of measuring theophylline can be carried in the usual manner for enzymatic determinations, including optimized pH and temperature ranges in which theophylline utilizing enzymes are active. Moreover, such determinations are preferably carried out in a buffered environment.

A method of obtaining theophylline utilizing or recognizing enzymes is also disclosed herein (and is described in detail hereinafter) and can be used to obtain such enzymes. In principle, all variants of theophylline utilizing enzymes which can be used for the enzymatic determination of theophylline fall within the scope of the present invention.

The following represents various test systems wherein theophylline in a test sample can be determined using the methodology disclosed in the present specification:

1) Measuring the decrease of theophylline concentration in the system. In this system, the disappearance of the substrate theophylline can be measured by determining the decrease of absorbance at a wavelength of 272 nm, where theophylline has maximum absorbance. This is shown in Example 1 by using a theophylline oxidase and in Example 2 by using a theophylline dehydrogenase. However, this decrease is common to all reactions involving theophylline utilizing enzymes. This change can also be detected by measuring the reflectance, which is the inverse of the absorbance, or;

2) Measuring a change of the oxidation-reduction potential of the system in either of two ways, a) measuring a change in the enzyme or enzyme complex system itself, as shown in Example 3, wherein the enzyme spectrum, such as an absorption spectrum, changes in the presence of theophylline, as can be seen by the changes that occur at wavelength 410 nm and 550 nm or measuring changes electrochemically, or b) by a change of an electron carrier added to the system such as, for example, the reduction of ferricyanide to ferrocyanide. Example 4 shows the absorbance change at 410 nm that occurs when ferricyanide changes to ferrocyanide in the presence of the theophylline dehydrogenase enzyme as the reaction takes place. This change can also be measured by spectrophotometric or electrochemical methods, or;

3) Measuring the appearance of any product associated with the enzymatic reaction of theophylline. The products produced in this reaction vary with the particular enzyme involved. For example, an enzyme can recognize theophylline sufficiently and react by oxidizing, dehydrogenating or demethylating theophylline. Example 5 shows the appearance and measurement of formaldehyde when theophylline demethylase was used. Example 6 shows the appearance and measurement of hydrogen peroxide when theophylline oxidase was used.

The product formation can be further illustrated by the following reactions or processes:

i) When the enzyme is capable of oxidizing theophylline and converts theophylline (1,3 dimethyl xanthine) to 1,3 dimethyl uric acid utilizing oxygen as an electron acceptor. This is diagrammatically shown as follows:

theophylline + $O_2$ + $H_2O$ $\xrightarrow{\text{theophylline oxidase}}$ 1,3 dimethyl uric acid + hydrogen peroxide In this system, the hydrogen peroxide thus produced can be determined titrimetrically, potentiometrically, polarographically, colorimetrically as well as enzymatically. The enzymatic methods of measuring hydrogen peroxide are preferred since they are not only specific and reliable, but can also be combined in a simple way with the hydrogen peroxide of the above reaction to produce color. For example, a peroxidase method is described in *Anal. Biochem.*, 105, 389, (1980). Using theophylline oxidase, Example 6 demonstrates that the hydrogen peroxide formation is proportional to the concentration of theophylline in the sample and can, therefore, be used for the quantitation of theophylline. Alternatively, the rate of oxygen consumption in accordance with the above general equation can be measured, for instance, by gas chromatography and depolarization methods. The depolarization method utilizing oxygen electrodes (available from Yellow Spring Instruments, Yellow Spring, Ohio) is well known and also described in U.S. Pat. No. 3,838,011 and in *J. Appl. Physiol.*, 18, 1247 (1963).

ii) When the enzyme uses an acceptor other than oxygen such as ferricyanide, NAD, cytochromes, etc. to oxidize theophylline and produces 1,3 dimethyl uric acid and a reduced acceptor in the following manner:

theophylline + oxidized acceptor $\xrightarrow{\text{theophylline dehydrogenase}}$ 1,3 dimethyl uric acid + reduced acceptor In such a system, the product 1,3 dimethyl uric acid can be measured or determined by several methods. Example 7 describes one in which the absorbance at 292 nm is determined using theophylline dehydrogenase. At such wavelength, 1,3 dimethyl uric acid absorbs optimally. Again, the increase in absorbance was found to be proportionate to the theophylline concentration in the sample and can, therefore, be used for the quantitation of theophylline.

Moreover, the concentration of theophylline in the sample can be determined using this reaction scheme by measuring the oxidation/reduction state of the electron acceptors used. Examples 4 and 8 show a test method where ferricyanide is used as an acceptor and is reduced to ferrocyanide by theophylline dehydrogenase. In Example 4, the decrease of ferricyanide is determined by measuring the decrease in absorbance at 410 nm wavelength as ferricyanide maximally absorbs at 410 nm and ferrocyanide has no absorption at that wavelength. It was again found that the decrease in absorbance was proportionate to the concentration of theophylline in the sample. In Example 8, another way of measuring ferrocyanide is shown. In this scheme, the formation of ferrocyanide is measured chemically by using 4,7 diphenyl-1,10 phenanthroline sulfonate by the method described by Avon, M. and Shavit N., *Analy. Biochem.*, 6, 549 (1963). The Avon method produced color which was measured at 535 nm. The color thus produced was proportionate to the concentration of theophylline in the sample.

Example 9 illustrates the use of another electron acceptor, ferricytochrome c. In this example ferricytochrome c is reduced to ferrocytochrome c. The appearance of ferrocytochrome c is measured by measuring the increase in absorbance at 550 nm wavelength in the presence of theophylline dehydrogenase. Again, the change in absorbance at 550 nm wavelength was found to be proportionate to the concentration of theophylline in the sample.

Similarly, one can use other known electron acceptors, sucu as nicotinamide adenine dinucleotide (NAD), 2,6-dichlorophenolindophenol (DCPIP), phenazine methosulfate (PMS), etc.

In all examples shown, one can also measure the change in reflectance as reflectance is inversely proportionate to absorbance.

The measurement of the change produced by the transferring of electrons in the above reaction is by no means limited to the spectrophotometric or reflectance methods. It is well known to use potentiometric, fluorescent or electrochemical methods to measure the transfer or change of electrons in oxidation-reduction reactions. For example, Reed and Hawkredge have shown an electron transfer reaction of cytochrome c at silver electrodes in *Anal. Chem.*, 59, 2334 (1987) which can be used with the present invention to measure the change of cytochrome c that occurs. Also, ferrocene or ferrocene derivatives have been used as electron acceptors for electrochemical methods as reported in the U.S. Pat. No. 4,545,382. These acceptors can also be used in the present enzymatic theophylline measurement and the change measured electrochemically. Also, the change of ferricyanide to ferrocyanide can be determined by measuring the change in current using platinum electrodes as has been established and reported in *Anal. Chem.*, 36, 343 (1964).

iii) when the enzyme is capable of demethylating theophylline by cleaving either one or both methyl groups. When one methyl group is cleaved, it produces either 1-methyl xanthine or 3-methyl xanthine along with 1 mole of formaldehyde. When both methyl groups are cleaved, it produces xanthine and 2 moles of formaldehyde. The reaction is shown below:

theophylline + NADPH + O$_2$ $\xrightarrow{\text{theophylline demethylase}}$ 1 methyl xanthine + formaldehyde + NADP and/or

3 methyl xanthine + formaldehyde + NADP and/or xanthine + formaldehyde + NADP In the above reaction, NADPH is shown as electron donor. However, there are other electron donors, such as NADH or FADH, which can also be used. The formaldehyde reaction product can be measured by customary and already known chemical, enzymatic, or electrochemical methods. Example 5 shows one method of measuring formaldehyde when theophylline demethylase was used. As indicated in the Example, the formaldehyde thus produced was proportionate to the concentration of theophylline in the sample and can, therefore, be used for the quantitation of theophylline.

The reaction products xanthine or methyl xanthine can also be measured as indicated below:

xanthine (or methyl xanthine) + O$_2$ $\xrightarrow{\text{xanthine oxidase}}$ uric acid (or methyl uric acid) + H$_2$O$_2$ The hydrogen peroxide (H$_2$O$_2$) formed can be measured by various methods as mentioned earlier, while uric acid or methyl uric acid can be measured, for example, by determining the increase in absorbance at 292 nm wavelength or colorimetrically as described in *Clin. Chem.*, 26, 227 (1980).

The decrease of NADPH or NADH can also be measured spectrophotometrically or fluorometrically by customary methods as described in *Anal. Biochem.*, 12, 357 (1965). The decrease of FADH can be measured by measuring the decrease at 450 nm wavelength as shown in *J. Biol. Chem.*, 246, 2371 (1971).

iv) other products produced by the enzymatic recognition of theophylline and measured by customary methods such as spectrophotometric, electrochemical or chromatographic or alternatively by a decrease in theophylline concentration as in Example 1.

In addition to the liquid test reactions disclosed herein, the test reagent compositions and devices of the present invention can contain state of the art additives and adjuvants which are advantageous to the reaction, such as, for example, buffers, suspending agents, thickening agents, color enhancers, surfactants, and so forth.

Moreover, in addition to the liquid reagent test systems described previously, the compositions of the present invention can advantageously be incorporated into solid carriers or matrices. Such a configuration or format is referred to in the art as dry-chemistry or solid state test device formats. The most common matrix is paper; however, other bibulous materials such as polymers, clays, gels and so forth may be utilized. Basically, the reagent composition is incorporated or impregnated into the matrix and dried. In use, the device is either dipped into or contacted with the sample being tested. The signal generated in the device by the reaction of theophylline with the test composition containing, inter alia, theophylline utilizing enzyme can then be detected and quantified using state of the art techniques, such as, for example, visual comparison to a color chart, reflectance spectrophotometry, and so forth. Example 10 shows the device resulting from impregnating a filter paper with theophylline dehydrogenase and cytochrome c. The change in color with increasing concentration of theophylline can be read semi-quantitatively by visual inspection or quantitatively by existing reflectance measuring instruments. Alternatively, the change in electron transfer in a solid matrix can be measured electrochemically. In the above reaction, cytochrome c can be replaced by other indicators such as NBT, MTT, etc.

In summary, all the examples mentioned above and described below show that this enzymatic approach for the determination of theophylline allows the production of an easy and convenient test format not only in a liquid system but also in a solid matrix test device.

The microbial enzymes used in the method of the present invention were obtained as follows. Using the following procedures, surprisingly, micro-organisms were found which contain enzymes which recognize theophylline sufficiently and utilize theophylline as a substrate.

Approximately two hundred and fifty micro-organisms were tested for the presence of theophylline utilizing or recognizing enzymes. Each micro-organism was streaked on a plate consisting of a sterile media composed of 0.1% purines, such as theophylline, salt solution, (salt solution containing per liter: 6.8 g $KH_2PO_4$, 7.1 g $Na_2HPO_4$, 0.2 g $MgSO_4.7H_2O$, 0.1 mg $MnCl_2.4H_2O$, 0.2 mg $FeSO_4.7H_2O$, 0.2 mg $(NH_4)_2SO_4$, 2.0 mg $CaCl_2$, 1 gm $NH_4Cl$, adjusted to pH 6.8 using potassium hydroxide) and 2% agarose. The plates were incubated at 30/C for 48 to 72 hours. The micro-organisms which grew on these plates were transferred to 250 mL erlenmeyer flasks containing 50 mL of media. This media contained 0.1% purines, such as theophylline, 1% yeast extract, and salt solution. The flasks were placed in a shaker and stirred at 200 rpm at 30° C. The micro-organisms thus grown served as an inoculum for 2.8 L flasks containing 1 L of growth media of the same composition as mentioned above. The 2.8 L flasks were shaken at 30° C. for 36 to 48 hours at 200 rpm. The cells were harvested by centrifugating the grown media at 10,000 g for 30 minutes. The cells were suspended in 0.1M potassium phosphate buffer, pH 7.0, containing 0.1 mM EDTA at the concentration of 1 g per 10 mL of buffer. The cells were broken using a french press at 15,000 psi. The supernatant was collected by centrifugation at 15,000 g for 30 minutes. The supernatant, also referred to as crude extract (S1), thus obtained from each micro-organism was checked for theophylline recognizing or utilizing enzyme activity by using the following assay procedures.

ASSAY FOR THEOPHYLLINE OXIDASE

Reaction 1

Theophylline + $O_2$ $\xrightarrow{\text{Enzyme}}$ 1,3 dimethyluric acid + $H_2O_2$ In a cuvette containing 0.5 mL of buffer, 0.1 potassium phosphate, pH 7.0, and 0.1 mM theophylline, 25 μL of crude enzyme (S1) was added and the decrease of absorbance at 273 nm wavelength was measured. As theophylline has a maximum absorption at 273 nm wavelength, the decrease of absorption at 273 nm indicates the presence of theophylline recognizing or utilizing enzymes as depicted in Reaction 1.

The reaction was also confirmed by simultaneously following the increase in absorbance at 293 nm where the reaction product 1,3 dimethyluric acid typically absorbs.

Furthermore, as Reaction 1 produced hydrogen peroxide, and as the measurement of $H_2O_2$ confirms the presence of theophylline oxidase, the crude extract (S1) was tested for theophylline oxidase activity using a $H_2O_2$ assay as follows:

The assay mixture contained 0.1M potassium phosphate, pH 7.5, 10 mM theophylline, 14 mM phenol, 0.015%, 4-aminoantipyrine, and 18 U/mL horseradish peroxidase. The assay was run at 37° C. The increase in absorbance was measured at 500 nm wavelength. The enzyme activity was calculated as the formation of 1 μmole of $H_2O_2$ per minutes at 37° C.

$$\text{Activity U/mL} = \frac{\Delta OD_{500}/\text{mixture} \times \text{total assay volume} \times \text{dilution}}{5.33 \times \text{sample volume}}$$

This assay provided the quantitative measurement of theophylline oxidase in crude extracts prepared from the various organisms.

ASSAY FOR THEOPHYLLINE DEHYDROGENASE

Theophylline recognizing or utilizing enzymes were shown to be present by using other assays. When crude extract samples were found which showed the utilization of theophylline by exhibiting a decrease in absorbance at 273 nm or increase in absorbance at 293 nm wavelength but did not produce hydrogen peroxide, they were checked for theophylline dehydrogenase activity (i.e., oxidation of theophylline in the presence of an electron acceptor other than oxygen). Various electron acceptors such as potassium ferricyanide, NAD, and cytochrome c, were used in assaying crude extracts for dehydrogenase activity. The theophylline dehydrogenase reactions are depicted in Reaction 2.

Reaction 2 a) Potassium Ferricyanide as an electron acceptor

If the crude extract (S1) contains theophylline dehydrogenase and potassium ferricyanide is used as an electron acceptor, the potassium ferricyanide will be converted to potassium ferrocyanide. The potassium ferrocyanide is detected and measured by measuring the decrease in absorbance (or optical density) at 410 nm wavelength.

The assay mixture contained 0.05M potassium phosphate buffer at pH 7.0, 50 μL of crude extract (S1), and 1.40 mM potassium ferricyanide. The reaction was carried out in a Gilford spectrophotometer with 10 mm light path at 30° C. The decrease in absorbance at 410 nm indicates the presence of theophylline dehydrogenase activity. Dehydrogenase activity was quantitated by the following calculation.

$$\text{Activity U/mL} = \frac{\Delta OD_{410}/\text{minute} \times \text{total reaction volume} \times \text{dilution}}{1.0 \times \text{volume of sample (mL)}}$$

b) NAD as an alternate electron acceptor

The method was the same as above except that the reaction mixture contained 1 mM NAD instead of potassium ferricyanide. The reaction was followed at 30° C. and the appearance of NADH was measured by following the increase in absorbance at 340 nm wavelength. The dehydrogenase activity was quantitatively calculated as:

$$\text{Activity U/mL} = \frac{\Delta OD_{340}/\text{minute} \times \text{total reaction volume} \times \text{dilution}}{6.22 \times \text{volume of sample (mL)}}$$

c) Cytochrome c as an alternate electron acceptor

The method was the same as above except the reaction mixture contained 25 nmoles cytochrome c instead of potassium ferricyanide. The reaction was followed at 30° C. and the appearance of reduced cytochrome was detected and followed by measuring the increase in absorbance at 550 nm wavelength. The dehydrogenase activity was quantitatively calculated as:

$$\text{Activity U/mL} = \frac{\Delta OD_{550}/\text{minute} \times \text{total reaction volume} \times \text{dilution}}{20.0 \times \text{volume of sample (mL)}}$$

In all cases the unit activity of the enzyme was defined as: 1 unit of enzyme utilizes 1 μmole of substrate (theophylline) per minute or 1 μmole of product is formed per minute under the given assay conditions.

THEOPHYLLINE DEMETHYLASE ACTIVITY

As the presence of theophylline utilizing or recognizing enzyme in the crude extract does not have to only involve oxidation reactions as shown in Reactions 1 and 2, other assays were performed in the crude extract. Reaction 3 shows an example of other enzymatic reactions that can also take place and which can be used in the measurement of theophylline in the sample.

Reaction 3 where theophylline is demethylated in the presence of NADH or NADPH and is converted to methylxanthine or xanthine with formation of formaldehyde and NAD.

The crude extracts were tested for the presence of theophylline demethylase using the following procedure:

The assay mixture consists of 0.05M Tris-HCl, pH 8.0, buffer containing 0.4 mM NADH and 10 mM theophylline. The decrease in absorbance due to NADH utilization and the formation of NAD was measured at 340 nm wavelength at 30° C. (ΔOD sample). A blank rate was determined where the same assay mixture was used without theophylline (ΔOD blank). The difference between these two absorbancies, i.e., (ΔOD sample − ΔOD blank)/minute, is proportionate to the activity of theophylline demethylase present in the crude extract. Theophylline demethylase activity was calculated as:

$$\text{Activity U/mL} = \frac{(\Delta OD_{sample} - \Delta OD_{blank})/\text{min} \times \text{total reaction volume (mL)} \times \text{dilution}}{6.22 \times \text{sample volume (mL)}}$$

Crude extracts (S1) from over 22 micro-organisms showed theophylline utilizing or recognizing activity. Most of these crude extracts were identified to contain oxidase, dehydrogenase, or demethylase activity. However, three micro-organisms used theophylline as a substrate and showed a decrease in absorption at 273 nm wavelength but could not be specifically identified to carry out oxidation, demethylation, or dehydrogenation suggesting that these samples contained some other theophylline recognizing or utilizing enzymes which could be used for determining the concentration of theophylline.

Three micro-organisms were selected whose crude extracts (S1) showed the most activity/mL and which belonged to one class of microbial enzyme, i.e. oxidase, dehydrogenase, or demethylase. The micro-organisms producing maximum demethylase activity, maximum oxidase activity, and maximum dehydrogenase activity were selected, denominated T-040, T-060 and T-090, respectively, and were deposited on Aug. 10, 1990 at NORTHERN REGIONAL RESEARCH LABORATORY, Peoria, Ill., where they were given the deposit numbers NRRL B-18697, NRRL B-18698, and NRRL B-18699, respectively.

PURIFICATION OF ENZYMES

The enzymes—theophylline demethylase from T-040 organism, theophylline oxidase from T-060 organism, and theophylline dehydrogenase from T-090 organism—were isolated and partially purified. The partially purified enzymes demethylase, oxidase, and dehydrogenase were identified as T-040, T-060, and T-090, respectively, and called as a group theophylline utilizing enzymes which were used in determining the concentration of theophylline in a given sample.

The enzymes were partially purified using well established biochemical techniques. The same common method, as described below, was used.

Step 1) Crude extracts were prepared by the procedure described earlier. The method involved growing respective organisms in 50 L media, collecting the organisms by centrifugation, suspending the organisms in a buffer medium (10 mM potassium phosphate buffer, pH 7.5, containing 2 mM EDTA), breaking the cells by homogenization using a french press or Menton-Gaulin homogenizer, and collecting the crude extract by centrifugation.

Step 2) DEAE ion-exchange chromatography: the crude extracts were checked for the respective enzyme activity. A column of 5×100 cm with a bed volume of approximately 2 L capacity was packed with Pharmacia DEAE-sepharose resin, which was previously equilibrated with 10 mM potassium phosphate, pH 7.5, containing 2 mM EDTA. The crude extract, approximately 5 liters, was diluted to the same ionic strength with deionized water and charged to the above DEAE column. After loading the enzyme, 10 L of equilibrating buffer was passed through the column. Subsequently, the column was eluted with 6 liters of equilibrating buffer containing 50 mM NaCl, 100 mM NaCl, 150 mM NaCl, and 200 mM NaCl as a step-wise gradient. The fractions were collected in 20 mL volumes in a LKB fraction collector. Each fraction was checked for enzyme activity and the protein content was determined by measuring $OD_{280}$. The fractions with maximum specific activity, activity/mL ÷ mg protein/mL were pooled, and rechecked for activity. Demethylase activity appeared in fractions when the column was eluted with eluting buffer containing 100 mM NaCl, oxidase activity appeared in fractions when the column was eluted with eluting buffer containing 150 mM NaCl, and dehydrogenase activity appeared in fractions when the column was eluted with eluting buffer containing 50 mM NaCl.

Step 3) Concentration of enzymes: each enzyme was concentrated using ultrafiltration method with a membrane cut off of 10,000 molecular weight (PM-10 membrane from Amicon). The concentrated enzymes were checked for activity/mL (10-20 U/mL), protein, and specific activity (0.5-2.0 U/mg protein). The enzymes were stored at $-20°$ C. in a freezer in small portions and were used for the estimation of theophylline in samples in a manner similar as shown in the following examples.

EXAMPLES

The following examples are intended for illustration of the present invention and are not intended to limit the scope thereof.

In all the examples given herein, the enzyme activity is defined as 1 μmole of theophylline utilized per minute at 30° C. temperature unless specified otherwise.

EXAMPLE 1

The assay mixture contained 0.05M potassium phosphate buffer, pH 7.0, and 0.4 u/ml of a theophylline utilizing or recognizing enzyme, such as theophylline oxidase. To 2 ml assay mixture, 100 μl of a sample containing theophylline at several concentrations was added in separate cuvettes. The reaction was carried out in a Gilford spectrophotometer with 10 mm light path cuvette at 30° C. A decrease in optical density at 272 nm was observed after 30 minutes which was proportionate to the theophylline concentration in the sample.

| Theophylline concentration | Decrease in OD at 272 nm |
| --- | --- |
| 40 mg/L | .067 |
| 20 mg/L | .033 |
| 10 mg/L | .017 |

EXAMPLE 2

The assay mixture contained 50 μmoles/ml potassium phosphate buffer at pH 7.5 and 1.8 u/ml of a theophylline utilizing or recognizing enzyme, such as theophylline dehydrogenase and 25 nmoles/ml of cytochrome c. To 0.5 ml assay mixture, 25 μl of a sample containing theophylline at the concentrations below were added in separate cuvettes. The reaction was carried out in a Gilford spectrophotometer with 10 mm light path cuvette at 30° C. After 20 minutes, the decrease in optical density at 272 nm was recorded which was proportionate to the theophylline concentration in the sample.

| Theophylline Concentration | Decrease in OD at 272 nm |
| --- | --- |
| 40 mg/L | 0.065 |
| 20 mg/L | 0.031 |
| 10 mg/L | 0.015 |

EXAMPLE 3

Figure 1:
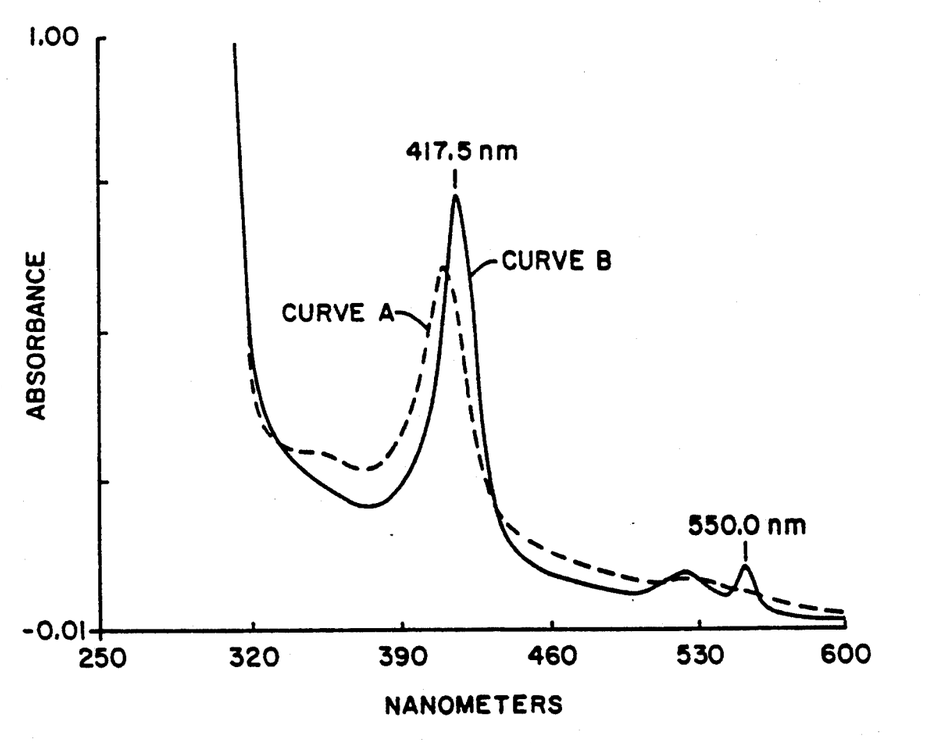

In this example, theophylline dehydrogenase was used. As shown in the Figure, Curve A describes the absorbance spectra of theophylline dehydrogenase at a concentration of 1.8 u/ml in 0.05M potassium phosphate buffer at pH 7.5. Curve B shows the absorbance spectra of the enzyme in the presence of theophylline at the concentration of 2 mg/L under the same conditions.

As can be seen, theophylline caused the increase in absorbance at 417.5 and 550 nm wavelength. These changes in absorptions are used as a basis for the determination of theophylline concentration in a sample.

EXAMPLE 4

In this example, theophylline dehydrogenase was used with potassium ferricyanide as an acceptor. The potassium ferricyanide changed to ferrocyanide in the presence of the enzyme when theophylline was added. The formation of ferrocyanide can be measured by measuring the decrease in optical density at 410 nm.

The assay mixture contained 50 μmoles/ml of potassium phosphate buffer, 1.8 u/ml of theophylline enzyme, and 1.43 μmoles/ml of potassium ferricyanide. To 0.35 ml assay mixture, 50 μl of a sample containing theophylline at the concentrations below was added in separate cuvettes. The reaction was carried out in a Gilford spectrophotometer with 10 mm light path cuvette at 30° C. After 30 minutes, the decrease in optical density at 410 nm wavelength was measured which was proportionate to the concentration of theophylline in the sample.

| Theophylline Concentration | Decrease in OD at 410 nm |
| --- | --- |
| 40 mg/L | 0.141 |

-continued

| Theophylline Concentration | Decrease in OD at 410 nm |
| --- | --- |
| 30 mg/L | 0.109 |
| 20 mg/L | 0.076 |
| 10 mg/L | 0.047 |

EXAMPLE 5

In this example, theophylline demethylase was used. In the presence of NADPH or NADH, this enzyme demethylated theophylline and produced xanthine and/or 1 and/or 3 methyl xanthine and formaldehyde. The formaldehyde was measured by a known chemical method as reported by Nash, *Biochem. J.*, 55, 416–421 (1953). The formaldehyde production was proportionate to the concentration of theophylline in the sample.

The assay mixture contained 50 μmoles/ml of Tris-HCL buffer pH 8.0, 1 μmole/ml of NADPH and 10 nmoles/ml of semicarbazide. To 2.0 ml of assay mixture in a test tube, 2.5 units of theophylline demethylase was added. After the reaction mixture was shaken at 30° C. for 15 minutes, the reaction was stopped by adding 0.6 ml of 20% zinc sulfate, 0.66 ml of saturated barium hydroxide and allowing the mixture to stand 10 minutes at room temperature. The tubes were centrifuged at 8,000 g for 10 minutes. To 1.0 ml of supernatant, the following additions were made; 0.4 ml of Nash reagent (150 g ammonium acetate and 2 ml acetyl acetone in 500 ml of deionized water) and the tubes incubated at 60° C. in a water bath for 30 minutes. Absorbance was immediately read at 415 nm wavelength.

| Theophylline Concentration | Decrease in OD at 415 nm |
| --- | --- |
| 180 mg/L | 1.481 |
| 40 mg/L | 0.269 |
| 20 mg/L | 0.140 |
| 10 mg/L | 0.075 |

EXAMPLE 6

In this example, theophylline oxidase was used which produced 1,3 dimethyl uric acid and hydrogen peroxide in the presence of theophylline. The hydrogen peroxide was measured by a known modified Trinder's method as described by Fossati et al., *Clin. Chem.*, 26, 227 (1980).

The assay mixture contained 50 μmoles/ml potassium phosphate, pH 7.5, 5 μmoles/ml of 3,5-dichloro-2-hydroxy benzene sulfonate hydrochloride (DHBS), 1 μmole/ml 4-aminoantipyrine, 5.0 u/ml of horseradish peroxidase and 0.7 u/ml of theophylline oxidase. To 0.7 ml assay mixture, 50 μl of a sample containing theophylline at the following concentrations was added in separate cuvettes. The reaction was carried out in a Gilford spectrophotometer with 10 mm light path cuvette at 37° C. After 20 minutes, the increase in optical density at 510 nm was measured.

| Theophylline Concentration | Increase in OD at 510 nm |
| --- | --- |
| 40 mg/L | 0.172 |
| 20 mg/L | 0.089 |
| 10 mg/L | 0.045 |

EXAMPLE 7

In this example, theophylline dehydrogenase was used with cytochrome c. In the presence of theophylline the reaction produced 1,3 dimethyl uric acid. This product was measured at 292 nm which is the wavelength of maximum absorbance for 1,3 dimethyl uric acid.

The assay mixture contained 50 μmoles/ml potassium phosphate buffer at pH 7.5, 1.8 u/ml of theophylline dehydrogenase and 25 nmoles/ml of cytochrome c. To 0.5 ml assay mixture, 25 μl of a sample containing theophylline at the following concentrations was added in separate cuvettes. The reaction was carried out in a Gilford spectrophotometer with 10 mm light path cuvette at 30° C. After 20 minutes, the increase in optical density at 292 nm was recorded which was proportionate to the theophylline concentration in the sample.

| Theophylline Concentration | Increase in OD at 292 nm |
| --- | --- |
| 40 mg/L | 0.162 |
| 30 mg/L | 0.125 |
| 20 mg/L | 0.087 |
| 10 mg/L | 0.036 |

EXAMPLE 8

In this example, theophylline dehydrogenase was used with potassium ferricyanide as an acceptor which produces potassium ferrocyanide in the presence of theophylline. The ferrocyanide thus produced is measured chemically by using 4,7 diphenyl-1,10 phenanthroline sulfonate as described by Avon and Shavit in *Anal. Biochem.*, 6, 549 (1963).

The assay mixture contained 50 μmoles/ml of potassium phosphate buffer at pH 7.5, 1.8 u/ml of theophylline dehydrogenase, and 1.43 μmoles/ml of potassium ferricyanide. To 0.35 ml assay mixture, 50 μl of a sample containing theophylline at the following concentrations was added. The reaction was carried out in a Gilford spectrophotometer with 10 mm light path cuvette at 30° C. for 30 minutes. From the above, 50 μl of assay mixture was mixed with 35 μl of deionized water and 150 μl of color producing reagent. The color producing reagent contains 1M sodium acetate, 0.066M citric acid, 0.00055M ferrichloride in 0.1M acetic acid, and 83.3 μg of 4,7-diphenyl-1,10 phenanthroline. After 6 minutes the absorbance was measured at 535 nm wavelength. The absorbance is proportionate to the concentration of theophylline.

| Theophylline Concentration | Increase in OD at 535 nm |
| --- | --- |
| 40 mg/L | 0.319 |
| 30 mg/L | 0.241 |
| 20 mg/L | 0.171 |
| 10 mg/L | 0.080 |
| 5 mg/L | 0.045 |

EXAMPLE 9

In this example, theophylline dehydrogenase was used with ferricytochrome c as an acceptor which produces 1,3 dimethyl uric acid and ferrocytochrome c in the presence of theophylline. The formation of ferrocytochrome c is measured by the increase in absorbance at 550 nm wavelength.

The assay mixture contained 50 μmoles/ml of potassium phosphate buffer at pH 7.5, 5 u/ml of theophylline dehydrogenase, and 0.25 nmoles/ml horse ferricytochrome c. To 0.5 ml assay mixture, 25 μl of sample containing theophylline at the following concentrations was added in separate cuvettes. The reaction was carried out in a Gilford spectrophotometer with 10 mm light path cuvette at 30° C. After 15 minutes, when the reaction was complete, the increase in optical density was measured. As in the other examples, the absorbance has a linear relationship to the concentration of theophylline in the sample.

| Theophylline Concentration | Increase in OD at 550 nm |
| --- | --- |
| 40 mg/L | 0.454 |
| 30 mg/L | 0.361 |
| 20 mg/L | 0.264 |
| 10 mg/L | 0.109 |
| 5 mg/L | 0.055 |

EXAMPLE 10

Ten by ten mm square filter paper was impregnated with a solution containing theophylline dehydrogenase at various concentrations. For example, 50 u of theophylline dehydrogenase in 0.05M phosphate buffer, pH 7.5. This solution also contained 1 μmole/ml of ferricytochrome c. The paper was dipped in the above solution and air dried. When 50 μl of serum containing different concentrations of theophylline, 5–40 mg/L, was added to the filter paper, increasingly deeper shades of pink appeared corresponding to the increasing theophylline concentration. The gradation of pink color allowed the estimation of the different theophylline concentrations.

The foregoing is intended as illustrative of the present invention but not limiting. Numerous variations and modifications may be effected without departing from the true spirit and scope of the invention.

What is claimed is:

1. A method for determining theophylline in a sample suspected of containing theophylline comprising the steps of:
   (a) contacting said sample with theophylline oxidase obtained from a microorganism in the absence of an added electron acceptor whereby a measurable signal is produced;
   (b) measuring said signal produced; and
   (c) correlating said signal to the concentration of theophylline in the sample.

2. The method according to claim 1 wherein the microorganism is deposited as NRRL B-18698.

3. The method according to claim 1 wherein the signal measured is a decrease in absorbance at wavelengths from 260 to 280 nm.

4. The method according to claim 1 wherein the signal measured is a signal produced by the presence of hydrogen peroxide.

5. The method according to claim 4 wherein the hydrogen peroxide is measured in the presence of a chromogen and peroxidase.

6. The method according to claim 5 wherein said chromogen is a combination of 4-aminoantipyrine and 3,5-dichlorohydroxy benzene sulfonate.

7. The method according to claim 1 wherein the signal measured results from the depletion of oxygen from the substrate.

8. The method according to claim 1 wherein the signal measured is the increase in absorbance at 285–305 nm from the presence of 1,3-dimethyl uric acid.

9. A method determining theophylline in a sample suspected of containing theophylline comprising the steps of:
   (a) contacting said sample with a microbial theophylline dehydrogenase whereby a measurable signal is produced;
   (b) measuring said signal produced; and
   (c) correlating said signal to the concentration of theophylline in the sample.

10. The method according to claim 9 wherein said microbial theophylline dehydrogenase is isolated from the microorganism NRRL B-18699.

11. The method according to claim 9 wherein an electron acceptor is present.

12. The method according to claim 9 wherein the signal measured is a decrease in absorbance at 260–280 nm.

13. The method according to claim 11 wherein the electron acceptor is selected from the group consisting of cytochromes, ferricyanides, dichlorophenolindophenol, nicotinamide adenine dinucleotide, phenazine methosulfate, NBT, MTT and methylene blue.

14. The method according to claim 9 wherein the signal measured is the increase in absorbance between 260–280 nm resulting from the production of 1,3-dimethyl uric acid.

15. The method according to claim 13 wherein the electron acceptor is cytochrome C and the presence of reduced cytochrome C is measured by measuring the increase in absorbance at 550 nm.

16. A method for determining theophylline in a sample suspected of containing theophylline comprising the steps of:
   (a) contacting said sample with a microbial theophylline demethylase whereby a measureable signal is produced;
   (b) measuring said signal produced; and
   (c) correlating said signal to the concentration of theophylline in the sample.

17. The method according to claim 16 wherein the microbial theophylline demethylase is obtained from the microorganism NRRL B-18697.

18. The method according to claim 16 wherein an electron donor is present.

19. The method according to claim 18 wherein said electron donor is selected from the group consisting of reduced nicotinamide adenine dinucleotide, reduced nicotinamide adenine dinucleotide phosphate and reduced flavine adenine dinucleotide.

20. A test composition for the determination of theophylline in a sample consisting essentially of a microbial theophylline dehydrogenase and an electron acceptor.

21. The test composition according to claim 20 wherein said electron acceptor is selected from the group consisting of cytochromes, ferricyanides, dichlorophenolindophenol, nicotinamide adenine dinucleotide, phenazine methosulfate, NBT, MTT and methylene blue.

22. The test composition according to claim 21 wherein said electron acceptor is potassium ferricyanide.

23. The test composition according to claim 21 wherein said electron acceptor is cytochrome c.

24. A test composition for the determination of theophylline in a sample consisting essentially of a microbial theophylline demethylase and an electron donor.

25. The test composition according to claim 24 wherein said electron donor is selected from the group consisting of reduced nicotinamide adenine dinucleotide, reduced nicotinamide adenine dinucleotide phosphate and reduced flavine adenine dinucleotide.

26. The test composition according to claim 25 wherein the electron donor is reduced nicotinamide adenine dinucleotide.

27. The test composition according to claim 25 wherein the electron donor is reduced nicotinamide adenine dinucleotide phosphate.

28. A test composition for the determination of theophylline in a sample consisting essentially of a microbial theophylline oxidase and a peroxidase.

29. The test composition according to claim 28 further including a chromogen.

30. The test composition according to claim 29 wherein said chromogen is 3,5-dichloro-2-hydroxy benzene sulfonate hydrochloride and 4-aminoantipyrine.

* * * * *